United States Patent [19]

Cielo et al.

[11] Patent Number: 4,874,948
[45] Date of Patent: Oct. 17, 1989

[54] METHOD AND APPARATUS FOR EVALUATING THE DEGREE OF CURE IN POLYMERIC COMPOSITES

[75] Inventors: Paolo Cielo, Montreal; Jean-Claude Krapez, Longueuil; Kenneth C. Cole, St-Hubert; Ghislain Vaudreuil, Boucherville, all of Canada

[73] Assignee: Canadian Patents and Development Limited, Ottawa, Canada

[21] Appl. No.: 138,072

[22] Filed: Dec. 28, 1987

[30] Foreign Application Priority Data

Dec. 29, 1986 [CA] Canada .................................. 526374

[51] Int. Cl.⁴ ............................................ G01N 21/00
[52] U.S. Cl. .................................. 250/341; 250/338.1; 374/53
[58] Field of Search ...................... 250/341, 340, 338.4, 250/338.3, 338.1, 358.1; 374/53

[56] References Cited

U.S. PATENT DOCUMENTS

| | | | |
|---|---|---|---|
| 3,524,983 | 8/1970 | Voelz | 250/341 |
| 4,421,424 | 12/1983 | Price et al. | 374/48 |
| 4,481,418 | 11/1984 | Vanzetti et al. | 250/338.1 |
| 4,556,326 | 12/1985 | Kitchen, III et al. | 374/45 |
| 4,566,806 | 1/1986 | DeBondt | 374/53 |
| 4,579,463 | 4/1986 | Rosencwaig et al. | 374/57 |
| 4,582,520 | 4/1986 | Sturm | 65/3.43 |

Primary Examiner—Janice A. Howell
Assistant Examiner—Constantine Hannaher
Attorney, Agent, or Firm—Foley & Lardner, Schwartz, Jeffery, Schwaab, Mack, Blumenthal & Evans

[57] ABSTRACT

The degree of cure in a polymeric composite is evaluated in a simple, rapid and non-destructive manner by heating a surface portion of the polymeric composite to substantially curing temperature, over a predetermined period of time, and continuously monitoring with a non-contact temperature sensor temperature fluctuations of the heated surface portion during the predetermined period of time to obtain data comprising surface temperature values measured as a function of time. By processing such data including comparing with a calibration reference, for example by providing a curve of the measured surface temperature values against time and comparing with a reference curve, one can evaluate the degree of cure of the polymeric composite.

63 Claims, 4 Drawing Sheets

METHOD AND APPARATUS FOR EVALUATING THE DEGREE OF CURE IN POLYMERIC COMPOSITES

BACKGROUND OF THE INVENTION

The present invention relates to a method and apparatus for evaluating the degree of cure in polymeric composites. More particularly, the invention is directed toward evaluating the degree of cure in carbon-fiber-reinforced plastics, in a rapid and non-destructive manner.

Many products are made from thermosetting resins because fiber-reinforced plastics, lacquers and adhesives based on these resins generally have improved mechanical and chemical properties. They exhibit good mechanical and thermal stability and resist a wide variety of highly reactive chemicals. As with many other polymeric materials, development and control of the manufacturing process require a monitoring of the degree of cure.

This is particularly true with respect to graphite-epoxy composites which are subjected to strict inspection procedures because of their increasing utilization as structural composites in safety related fields such as in the aerospace industry. The mechanical Properties of carbon-fiber-reinforced plastics structures are much affected by the degree of cure of the resin matrix both before and after processing. Before processing, the slightly precured prepreg sheets (i.e. epoxy pre-impregnated carbon fiber sheets) which are shipped to the manufacturer in refrigerated cells are normally inspected to verify that the required pre-cure level has not been exceeded. After lay-up and autoclave curing, the degree of polymerization must be sufficiently high to assure the required mechanical performance.

A number of approaches are possible to evaluate the degree of polymer cure, including spectroscopic, calorimetric, mechanical, electromagnetic or ultrasonic methods, the most widely used being the spectroscopic and the thermal techniques. Infrared spectroscopy can provide quantitative data concerning the amount of unreacted epoxy groups. For best results, measurements must be made in transmission and, in the case of cured composites, this requires destruction (e.g. grinding) of the sample. The spectroscopic diffuse reflectance method has the advantage of being noncontact and nondestructive, but is of limited value for light-absorbing materials such as graphite-epoxy composites.

Thermoanalytical methods include differential thermal analysis, differential scanning calorimetry, thermomechanical analysis and thermogravimetry techniques. The thermoanalytical approach is very powerful but rather time-consuming, requiring careful sample preparation and good thermocouple contact.

SUMMARY OF THE INVENTION

It is therefore an object of the present invention to overcome the above drawbacks and to provide a method and apparatus for evaluating the degree of cure in polymeric composites, in a simple, yet rapid and non-destructive manner.

It is a further object of the invention to provide such a method and apparatus: which also require no sample preparation and are relatively insensitive to the geometry of the polymeric composite under investigation.

In accordance with the present invention, there is thus provided a method of evaluating the degree of cure in a polymeric composite, which comprises the steps of:

(a) heating a surface portion of the polymeric composite to substantially curing temperature, over a predetermined period of time;

(b) continuously monitoring with a non-contact temperature sensing means temperature fluctuations of the heated surface portion during the predetermined period of time to obtain data comprising surface temperature values measured as a function of time; and (c) processing the data obtained in step (b) including comparing with a calibration reference to obtain an evaluation of the degree of cure of the polymeric composite.

The present invention also provides, in another aspect thereof, an apparatus for carrying out a method as defined above, which comprises:

heating means for heating a surface portion of the polymeric composite to substantially curing temperature, over a predetermined period of time; and non-contact temperature sensing means for continuously monitoring temperature fluctuations of the heated surface portion during the predetermined period of time to provide output signals representative of surface temperature values measured as a function of time, whereby upon processing such output signals including comparing with a calibration reference an evaluation of the degree of cure of the polymeric composite is obtained.

In step (a) of the method according to the invention, a surface portion of the polymeric composite is heated to substantially curing temperature, for example by a laser beam such as that generated by an argon-ion or $CO_2$ laser source. It is of course also possible to use any other type of radiative heat source, for example a heat lamp such as a quartz-halogen lamp. In the case where the polymeric composite inspected is a graphite-epoxy composite, a surface portion of such a composite is heated to a curing temperature typically in the range of from about 200° C. to about 300° C. over a period of time which may range from a few tens to several hundreds of seconds. Although such a temperature level is substantially higher than the recommended autoclave-curing temperature, it is sufficiently low to avoid major degradation of the heated surface.

The non-contact temperature sensing means which is used to continuously monitor the surface temperature fluctuations is advantageously an infrared detector having a surface sensitive to infrared radiation emanating from the heated surface portion of the polymeric composite. Such an infrared detector may comprise for example a InSb photodiode. Longer wavelength detectors such as a HgCdTe photodiode or uncooled devices such as a thermopile or a pyroelectric detector can be used as well for non-contact temperature sensing. Thus, no thermal flow from the heated surface to a bonded thermoelectric sensing device is involved, so that the true surface temperature is sensed without any thermal inertia.

According to a preferred embodiment of the invention, the heated surface portion has a center point thereof imaged onto the surface of the infrared detector by means of an imaging lens disposed between the heated surface portion and the infrared detector, for accurate temperature sensing.

According to a further preferred embodiment, a reflective, semi-spherical surface is positioned adjacent the heated surface portion in facing relationship to enhance surface absorptivity and emissivity conditions, the reflective surface having an aperture formed centrally thereof for allowing passage of radiation to and from the heated surface portion. Such an embodiment is particularly useful for low-absorptivity materials such as white-painted carbon-fiber-reinforced plastic structures or sandwich resin materials between aluminum sheets and enables to achieve nearly 100% surface absorptivity and emissivity conditions for quantitative analysis.

According to yet another preferred embodiment, the surface portion of the polymeric composite is heated by a laser beam travelling along an optical path and directed onto the surface portion, and an axicon lens is disposed in the optical path of the laser beam for providing uniform temperature distribution across the heated surface portion, the infrared radiation emanating from the heated surface portion being advantageously reflected onto the surface of the infrared detector by means of a dichroic mirror positioned in the optical path of the laser beam intermediate the axicon lens and the heated surface portion. The provision of an axicon lens or other beam-shaping conical optical elements enables to reduce the time-spread of the developed heat of reaction produced by a radially expanding polymerization ring.

In order to evaluate the degree of cure of the polymeric composite, the data obtained in step (b) of the method according to the invention and comprising surface temperature values measured as a function of time is suitably processed, for example by providing a thermogram curve of the measured surface temperature values against time and comparing with a reference curve. Since such a thermogram curve has a shape related to the degree of cure of the polymeric composite, one can thus evaluate the initial degree of cure from the shape of the thermogram curve as compared with the calibration reference. The reference curve may be that obtained under the same conditions with an inert material having the same geometry of the polymeric composite under investigation and undergoing no polymerization reaction.

Since the exact shape of the thermogram depends on a number of parameters such as the geometry and thermal anisotropy of the heated polymeric composite, the diameter surfaces losses, etc., an absolute analysis of a single thermogram should thus be repeated for every variation of the sample geometry or ambient ventilation level. In order to apply the method according to the invention to routine quality control in industry, such as on assembled parts of different geometries after autoclave curing, a differential approach is proposed by means of which it is possible to minimize changes in the thermogram shape related to variations of the part geometry or environmental conditions. According to such a differential approach, the same surface is repetitively submitted to heating cycles carried out at a same constant heating rate. The difference between the thermograms corresponding to two successive heating cycles gives a clear indication of whether the material has not yet completely cured or has completely cured.

Thus, according to a further preferred embodiment of the invention, the heated surface portion of the polymeric composite is allowed to cool to near ambient temperature and steps (a) through (c) are repeated at least once with the cooled surface portion being reheated at a same constant heating rate to obtain at least one further curve serving as calibration reference. This technique makes the measurement relatively insensitive to the geometry of the composite and environmental conditions.

A quantitative estimation of the fractional extent of curing of the inspected material requires a knowledge of the sample geometry and thermal properties in order to calculate the heat of polymerization reaction from the thermograms. Such a calculation can be made once and for all for a given geometry if the processed products have reproducible characteristics, or more simply an empirical calibration can be made on a series of samples whose degree of curing has been determined by a more quantitative physicochemical analysis.

The very small thermal inertia of the non-contact method according to the invention as compared to a thermal contact differential scanning calorimetry approach makes it possible to implement servo-loop, constant-surface-temperature techniques for reaction heat evaluation without risk of surface overheating. In such a case, the surface temperature is quickly raised to an optimum polymerization temperature at which the curing rate is as high as possible without reaching the thermal-damage threshold, and such a temperature is maintained during the observation period by suitably modulating the heat-source power using the temperature sensor output in a feedback loop. The time evolution of the heat-source power is thus monitored in this case.

Accordingly, the present invention further provides, in still another aspect thereof, a method of evaluating the degree of cure in a polymeric composite, which comprises the steps of:

(a) heating a surface portion of the polymeric composite to substantially curing temperature and maintaining such a temperature constant over a predetermined period of time;

(b) continously monitoring the amount of power required to maintain the heated surface portion at the constant temperature during the predetermined period of time to obtain data comprising power values measured as a function of time; and (c) processing the data obtained in step (b) including comparing with a calibration reference to obtain an evaluation of the degree of cure of the polymeric composite.

According to yet a further aspect of the invention, there is also provided an apparatus for carrying out a method as defined above, which comprises:

heating means for heating a surface portion of the polymeric composite to substantially curing temperature;

non-contact temperature sensing means for measuring the temperature of the heated surface portion to provide output signals representative of surface temperature values;

a feedback circuit connected between the heating means and the temperature sensing means, the feedback circuit having control means for controlling the heating means in response to the output signals provided by the temperature sensing means so as to maintain the curing temperature constant over a predetermined period of time; and monitoring means connected to an output of the control means for continously monitoring the amount of power required to maintain the heated surface portion at the constant temperature during the predetermined period of time, thereby obtaining data comprising power values measured as a function of time, whereby upon processing such data including comparing with a calibration reference an evaluation of the degree of cure of the polymeric composite is obtained.

Use is preferably made of an infrared detector for measuring the temperature of the heated surface portion. The latter is advantageously heated by a laser beam traveling along an optical path and directed onto the surface portion, the laser beam passing through a dichroic mirror disposed in the optical path thereof. A center point of the heated surface portion may thus be reflected by the dichroic mirror and imaged onto the surface of the infrared detector by means of an imaging lens positioned intermediate the dichroic mirror and the infrared detector.

Similarly as in the case involving surface temperature monitoring, evaluation of the degree of cure can be obtained by providing a curve of the measured power values against time, which curve has a shape related to the degree of cure of the polymeric composite, and evaluating the degree of cure from the shape of the curve as compared with the calibration reference. Preferably, the heated surface portion is allowed to cool to near ambient temperature, and steps (a) through (c) of the method are repeated at least once with the cooled surface portion being re-heated and maintained at the same constant temperature to obtain at least one further curve serving as calibration reference.

BRIEF DESCRIPTION OF THE DRAWINGS

Further features and advantages of the invention will become more readily apparent from the following description of preferred embodiments as illustrated by way of example in the accompanying drawings, in which.

DESCRIPTION OF PREFERRED EMBODIMENTS

Figure 1:
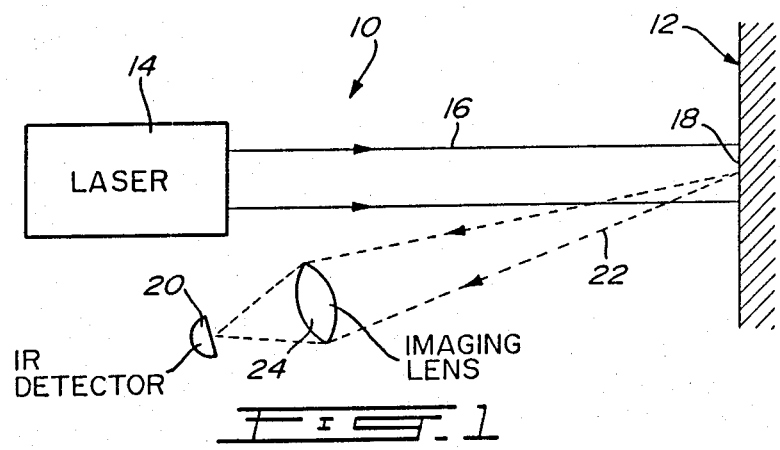
FIGS. 1 to 4 schematically illustrate different embodiments of an apparatus for evaluating the degree of cure in polymeric composites according to the invention.

Referring first to FIG. 1, there is illustrated an apparatus generally designated by reference numeral 10 for evaluating the degree of cure in a polymeric composite 12. As shown, the apparatus comprises a laser source 14 operative to generate a laser beam 16 directed onto a surface portion 18 of the polymeric composite 12 for heating the surface portion 18 to substantially curing temperature, over a predetermined period of time. The laser source 14 may be a 2 watts argon-ion laser or a 100 watts $CO_2$ laser. The temperature fluctuations of the heated surface portion 18 are continously monitored by means of an infrared detector 20 which is sensitive to the infrared radiation 22 emanating from the heated surface portion. In order to provide accurate temperature sensing, an imaging lens 24 is disposed between the heated surface portion 18 and the infrared detector 20 for imaging a center point of the heated surface portion 18 onto the surface of the infrared detector.

Figure 5:
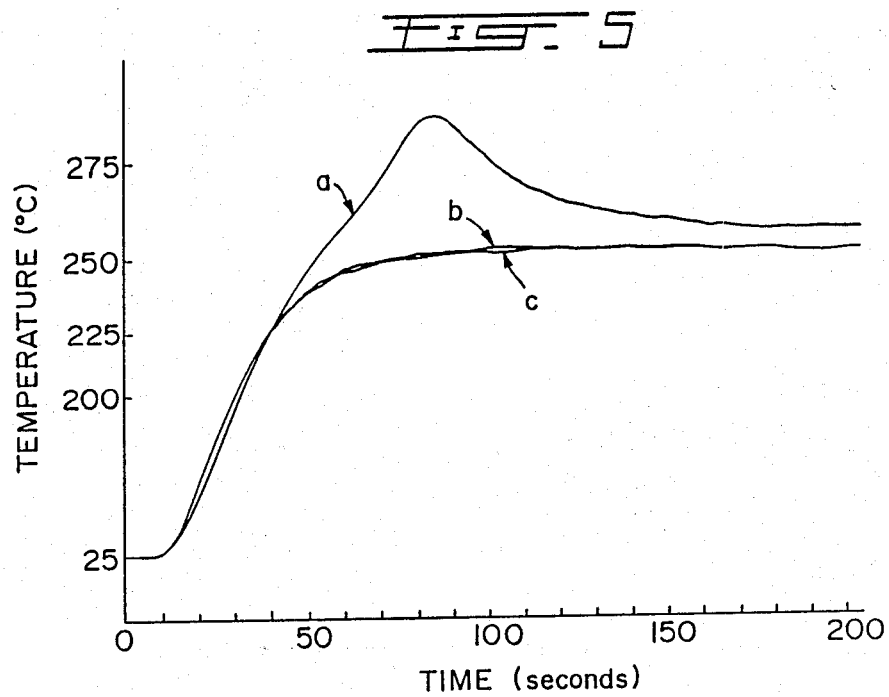
FIGS. 5 and 6 are plots of the measured surface temperature values against time, obtained from data provided by the apparatus shown in FIG. 1.

By plotting the measured surface temperature values against time as shown in FIG. 5, a thermogram curve is obtained having a shape related to the degree of cure of the polymeric composite. In the absence of exothermal reactions related to curing, and for a constant radiative heat input, the surface temperature increase as monitored by the infrared detector is of the kind of curves b or c in FIG. 5. The temperature stabilizes at a saturation temperature at which the heat input equals the conduction heat flow within the material plus the surface radiative and convective losses. In the case of a material which is at least partially uncured, a curve of the kind of curve a in FIG. 5 will be observed, the additional temperature level corresponding to the exothermal polymerization reaction. From the shape of the thermogram curve, one can thus evaluate the polymerization state of the material.

The three thermogram curves shown in FIG. 5 were obtained using the apparatus of FIG. 1, by repetitively submitting the same surface portion of a 1 mm-thick graphite-epoxy prepreg sheet to three heating cycles, with intermittent cooling to near ambient temperature between two successive heating cycles. Curves a, b and c correspond respectively to the first, second and third heating cycles. As shown, the difference between the thermograms corresponding to two successive heat cycles gives a clear indication of whether the material has not yet completely cured (curve a as compared with curve b) or has completely cured (curve b as compared with curve c).

Figure 6:
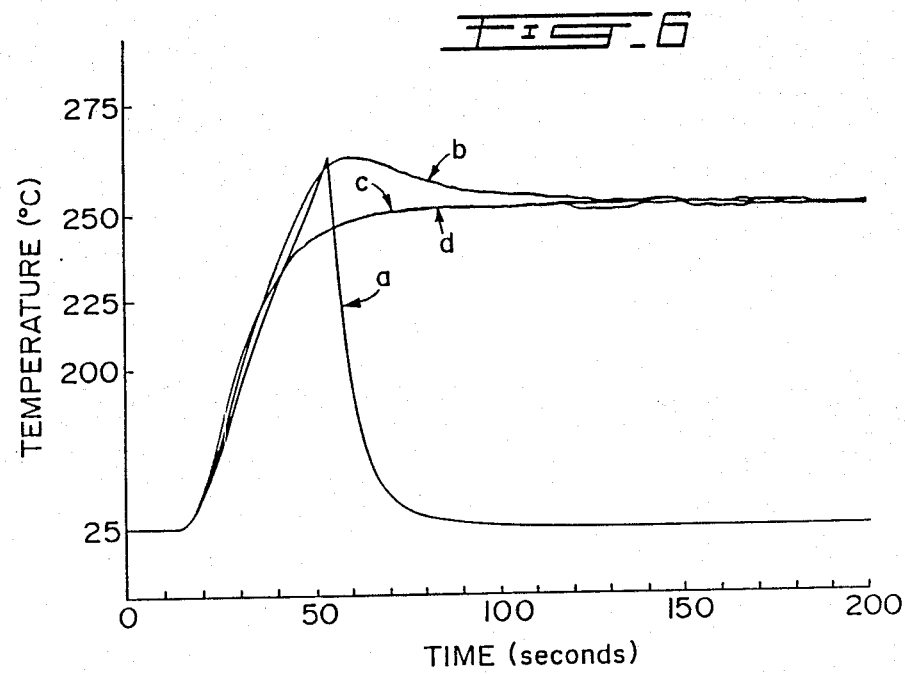

The behaviour of a prepreg sheet in a more advanced state of cure was also analysed by submitting a sample to a two-step sheeting cycles. The results are reported in FIG. 6. As shown, the first heating cycle (curve a) was interrupted to produce a partial polymerization of the prepreg sample. After cooling to near ambient temperature, a second heating cycle (curve b) was performed to complete the curing reaction, followed by two additional heat cycles (curves c and d) to be used as reference. The exothermal peak in curve b of FIG. 6 is significantly smaller than in the corresponding curve a of FIG. 5, indicating a more advanced polymerization state in the former case.

Figure 2:
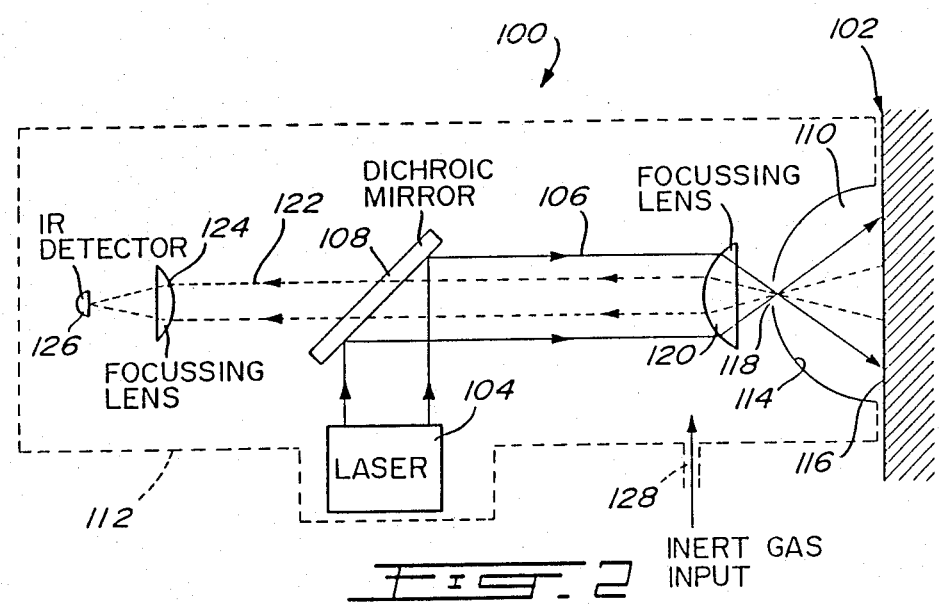

Turning to FIG. 2, there is illustrated an apparatus 100 which is especially adapted for evaluating the degree of cure of a low-absorptivity polymeric composite 102 such as a white-painted carbon-fiber-reinforced plastic structure or a sandwich resin material between aluminum sheets. As shown, the apparatus 100 comprises a laser source 104 operative to generate a laser beam 106 which is reflected by a dichroic mirror 108 in a direction toward a reflective cavity 110 formed at one end of the enclosure 112 and defined by a reflective, semi-spherical surface 114. The reflective surface 114 which is gold-plated is positioned adjacent the surface portion 116 of the polymeric composite 102 to be heated and in facing relationship so as to enhance surface absorptivity and emissivity conditions. An aperture 118 is formed centrally of the reflective surface 114 for allowing The laser beam 106 is focussed by a focussing lens 120 through the aperture 118 and onto the surface portion 116 for heating same. The infrared radiation emanating from the heated surface portion 116 and passing through the focussing lens 120 and dichroic mirror 108 is focussed by another focussing lens 124 onto the surface of the infrared detector 126. An inert gas can be injected through a suitable inlet 128 provided in the enclosure 112 for filling the latter and flowing through the aperture 118 into the reflective cavity 110. The provision of such a reflective cavity enables to achieve nearly 100% surface absorptivity and emissivity conditions for quantitative analysis.

Figure 3:
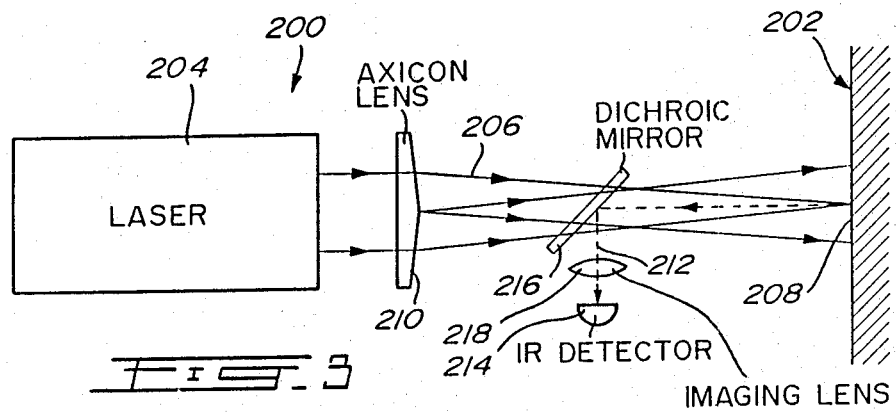

FIG. 3 illustrates another type of apparatus 200 for evaluating the degree of cure in a polymeric composite 202. The apparatus 200 comprises a laser source 204 for generating a laser beam 206 traveling along an optical path in a direction toward the surface portion 208 of the polymeric composite to be heated. An axicon lens 210 is disposed in the optical path of the laser beam 206 for providing uniform temperature distribution across the surface portion 208 heated by the laser beam 206. The infrared radiation 212 emanating from the heated surface portion 208 is reflected onto the surface of the infrared detector 214 by means of a dichroic mirror 216 positioned in the optical path of the laser beam 206 intermediate the axicon lens 210 and the heated surface portion 208. A center point of the heated surface portion 208 reflected by the dichroic mirror 216 is imaged onto the surface of the infrared detector 214 by means of an imaging lens 218 disposed between the dichroic mirror 216 and the infrared detector 214, to provide accurate temperature sensing.

Figure 7:
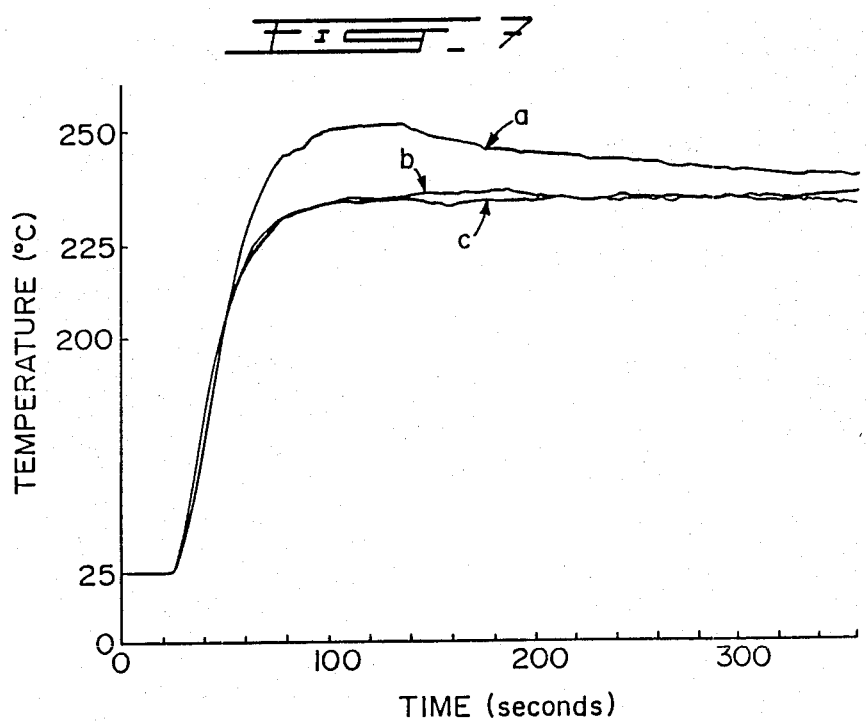
FIG. 7 is a plot similar to that shown in FIGS. 5 or 6, but obtained with a lower energy input.

The apparatus 200 illustrated in FIG. 3 is especially adapted for reducing the time spread of the developed heat of reaction produced by a radially expanding polymerization ring. An effect of this kind is shown in FIG. 7, where a lower heating temperature results in a lengthening of the exothermal peak because of a decrease in the reaction rate and of the radial expansion of the polymerizing volume; in FIG. 7, curves a, b and c correspond respectively to first, second and third heating cycles. The apparatus 200 enables one to overcome such a radial expansion of the polymerizing volume.

Figure 4:
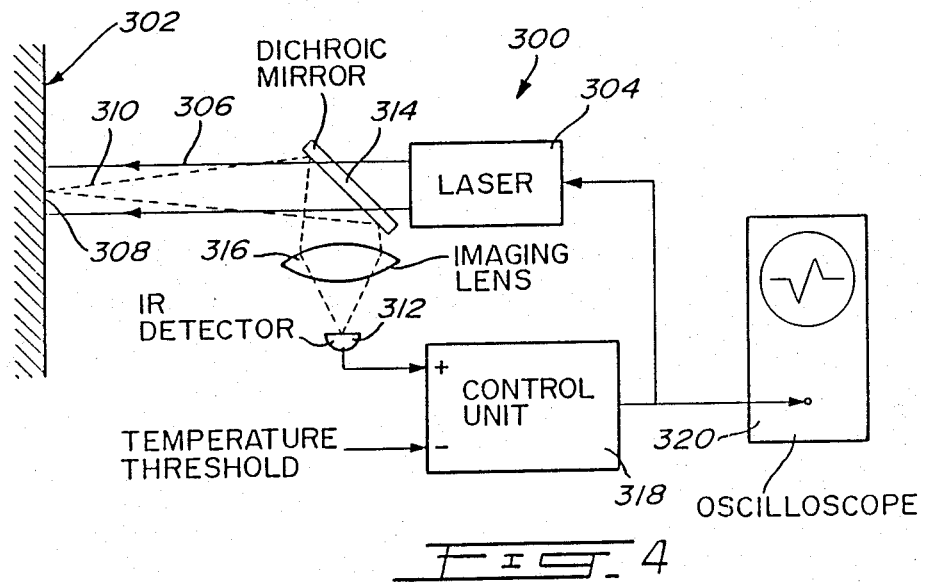

The apparatus 300 shown in FIG. 4 illustrates the implementation of a servo-loop, constant-surface-temperature technique for reaction-heat evaluation without overheating of the polymeric composite 302 inspected. As shown, the apparatus 300 comprises a laser source 304 operative to generate a laser beam 306 directed onto the surface portion 308 of the polymeric composite 302 for heating same. The infrared radiation 310 emanating from the heated surface portion 308 is reflected onto the surface of the infrared detector 312 by means of a dichroic mirror 314 disposed in the optical path of the laser beam 306. In order to provide accurate temperature sensing, a center point of the heated surface portion 308 reflected by the dichroic mirror 314 is imaged onto the surface of the infrared detector 312 by means of an imaging lens 316 positioned intermediate the dichroic mirror 314 and the infrared detector 312.

In order to maintain the heated surface portion 308 at a constant curing temperature, a feedback circuit having a control unit 318 is connected between the laser source 304 and the infrared detector 312. The control unit 318 which may be a proportional-integral-derivative programmable controller set for a stable temperature level (for example of 275° C. in the case of a graphite-epoxy composite) is operative to transmit a power regulating signal to the laser source 304 in response to the output signal of the infrared detector 312 so as to maintain the heated surface portion 308 at a constant curing temperature over a predetermined period of time. The amount of power required to maintain the heated surface portion 308 at constant temperature is continuously monitored by an oscilloscope 320 connected to the output of the control unit 318, thereby obtaining data comprising power values measured as a function of time.

Figure 8:
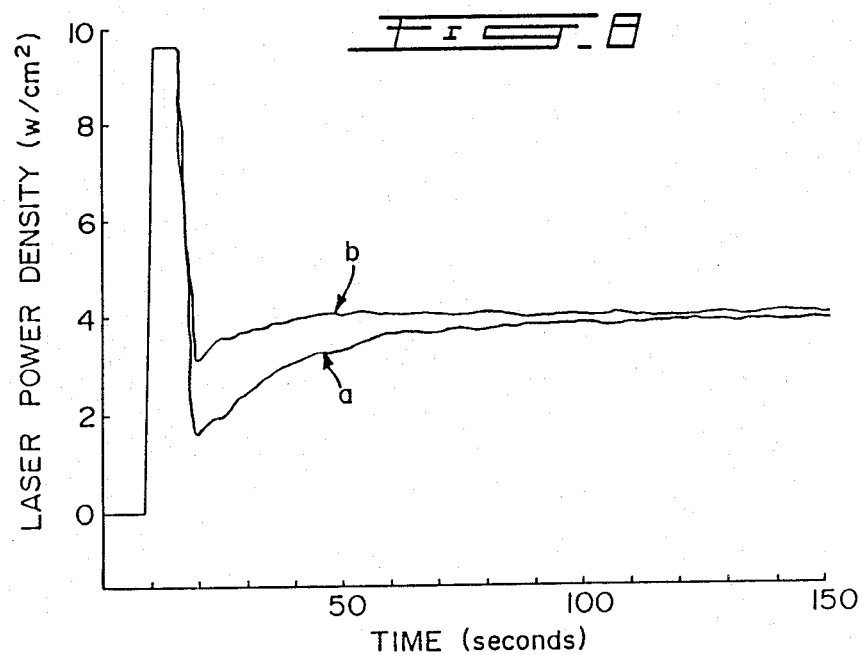
FIG. 8 is a plot of the measured power values against time, obtained from data provided by the apparatus illustrated in FIG. 4.

By providing a curve of the measured power values against time as shown in FIG. 8, one can evaluate the degree of cure from the shape of the curve as compared with a calibration reference. As shown, the difference between curve a (first heating cycle) corresponding to an uncured state and curve b (second heating cycle, used as reference) corresponding to a cured state is evident.

We claim:

1. A method of evaluating the degree of cure in a polymeric composite, which comprises the steps of:
   (a) heating a surface portion of the polymeric composite to substantially curing temperature, over a predetermined period of time;
   (b) continously monitoring with a non-contact temperature sensing means temperature fluctuations of the heated surface portion during said predetermined period of time to obtain data comprising surface temperature values measured as a function of time; and
   (c) processing the data obtained in step (b) including comparing with a calibration reference to obtain an evaluation of the degree of cure of said polymeric composite.

2. A method as claimed in claim 1, wherein said surface portion is heated by a laser beam.

3. A method as claimed in claim 2, wherein said laser beam is generated by an argon-ion or $CO_2$ laser source.

4. A method as claimed in claim 1, wherein said surface portion is heated by means of a heat lamp.

5. A method as claimed in claim 4, wherein said heat lamp is a quartz-halogen lamp.

6. A method as claimed in claim 1, wherein said non-contact temperature sensing means comprises an infrared detector having a surface sensitive to infrared radiation emanating from said heated surface portion.

7. A method as claimed in claim 6, wherein said infrared detector comprises a InSb photodiode.

8. A method as claimed in claim 6, wherein said heated surface portion has a center point thereof imaged onto the surface of said infrared detector by means of an imaging lens disposed between said heated surface portion and said infrared detector.

9. A method as claimed in claim 6, wherein a reflective, semi-spherical surface is positioned adjacent said heated surface portion in facing relationship to enhance surface absorptivity and emissivity conditions, said reflective surface having an aperture formed centrally thereof for allowing passage of radiation to and from said heated surface portion.

10. A method as claimed in claim 9, wherein said surface portion is heated by a laser beam directed through the aperture of said reflective surface and onto said surface portion, the infrared radiation emanating from the heated surface portion and passing through said aperture being focussed onto the surface of said infrared detector.

11. A method as claimed in claim 6, wherein said surface portion is heated by a laser beam travelling along an optical path and directed onto said surface portion, an axicon lens being disposed in the optical path of said laser beam for providing uniform temperature distribution across said heated surface portion, and wherein the infrared radiation emanating from the heated surface portion is reflected onto the surface of said infrared detector by means of a dichroic mirror positioned in the optical path of said laser beam intermediate said axicon lens and said heated surface portion.

12. A method as claimed in claim 1, wherein said noncontact temperature sensing means comprises a HgCdTe photodiode.

13. A method as claimed in claim 1, wherein said noncontact temperature sensing means comprises a thermopile.

14. A method as claimed in claim 1, wherein said noncontact temperature sensing means comprises a pyroelectric detector.

15. A method as claimed in claim 1, wherein step (c) is performed by providing a curve of the measured surface temperature values against time, said curve having a shape related to the degree of cure of said polymeric composite, and evaluating said degree of cure from the shape of said curve as compared with said calibration reference.

16. A method as claimed in claim 15, wherein said surface portion is heated at a constant heating rate.

17. A method as claimed in claim 16, wherein said heated surface portion is allowed to cool to near ambient temperature, and steps (a) through (c) are repeated at least once with the cooled surface portion being re-heated at the same constant heating rate to obtain at least one further curve serving as said calibration reference.

18. A method as claimed in claim 17, wherein steps (a) through (c) are repeated twice to provide a total of three heating cycles with intermittent cooling between two successive heating cycles, thereby obtaining three curves corresponding respectively to first, second and third heating cycles, and wherein the curve of the first heating cycle is compared with the curve of the second heating cycle, which itself is compared with the curve of the third heating cycle.

19. A method as claimed in claim 1, wherein said polymeric composite is a graphite-epoxy composite and said curing temperature is in the range of from about 200° C. to about 300° C.

20. An apparatus for evaluating the degree of cure in a polymeric composite, which comprises:
heating means for heating a surface portion of the polymeric composite to substantially curing temperature, over a predetermined period of time;
non-contact temperature sensing means for continuously monitoring temperature fluctuations of the heated surface portion to provide output signals representative of surface temperature values measured as a function of time; and
means for processing said output signals including comparing with a calibration reference to obtain an evaluation of the degree of cure of said polymeric composition.

21. An apparatus as claimed in claim 20, wherein said heating means comprises a laser source operative to generate a laser beam directed onto said surface portion for heating same.

22. An apparatus as claimed in claim 21, wherein said laser source is an argon-ion or $CO_2$ laser source.

23. An appratus as claimed in claim 20, wherein said heating means comprises a heat lamp.

24. An apparatus as claimed in claim 23, wherein said heat lamp is a quartz-halogen lamp.

25. An apparatus as claimed in claim 20, wherein said non-contact temperature sensing means comprises an infrared detector having a surface sensitive to infrared radiation emanating from said heated surface portion.

26. An apparatus as claimed in claim 25, wherein said infrared detector comprises a InSb photodiode.

27. An apparatus as claimed in claim 25, wherein an and said infrared detector for imaging a center point of said heated surface portion onto the surface of said infrared detector.

28. An apparatus as claimed in claim 25, wherein a reflective, semi-spherical surface is positioned adjacent said heated surface portion in facing relationship to enhance surface absorptivity and emissivity conditions, said reflective surface having an aperture formed centrally thereof for allowing passage of radiation to and from said heated surface portion.

29. An apparatus as claimed in claim 28, wherein said heating means comprises a laser source operative to generate a laser beam and wherein optical means are provided for directing said laser beam through the aperture of said reflective surface and onto said surface portion as well as for focussing onto the surface of said infrared detector the infrared radiation emanating from said heated surface portion and passing through said aperture.

30. An apparatus as claimed in claim 25, wherein said heating means comprises a laser source operative to generate a laser beam travelling along an optical path and directed onto said surface portion, an axicon lens being disposed in the optical path of said laser beam for providing uniform temperature distribution across the heated surface portion, and wherein a dichroic mirror is positioned in the optical path of said laser beam intermediate said axicon lens and said heated surface portion for reflecting the infrared radiation emanating from said heated surface portion onto the surface of said infrared detector.

31. An apparatus as claimed in claim 20, wherein said non-contact temperature sensing means comprises a HgCdTe photodiode.

32. An apparatus as claimed in claim 20, wherein said non-contact temperature sensing means comprises a thermopile.

33. An apparatus as claimed in claim 20, wherein said non-contact temperature sensing means comprises a pyroelectric detector.

34. An apparatus as claimed in claim 20, wherein said polymeric composite is a graphite-epoxy composite and wherein said heating means is operative to heat said surface portion to a curing temperature in the range of from about 200° C. to about 300° C.

35. A method of evaluating the degree of cure in a polymeric composite, which comprises the steps of:
(a) heating a surface portion of the polymeric composite to substantially curing temperature and maintaining said temperature constant over a predetermined period of time;
(b) continously monitoring the amount of power required to maintain the heated surface portion at said constant temperature during said predetermined period of time to obtain data comprising power values measured as a function of time; and
(c) processing the data obtained in step (b) including comparing with a calibration reference to obtain an evaluation of the degree of cure of said polymeric composite.

36. A method as claimed in claim 35, wherein said surface portion is heated by a laser beam.

37. A method as claimed in claim 36, wherein said laser beam is generated by an argon-ion or $CO_2$ laser source.

38. A method as claimed in claim 35, wherein said surface portion is heated by means of a heat lamp.

39. A method as claimed in claim 38, wherein said heat lamp is a quartz-halogen lamp.

40. A method as claimed in claim 35, wherein the temperature of said heated surface portion is measured by means of a non-contact temperature sensing means.

41. A method as claimed in claim 40, wherein said noncontact temperature sensing means comprises an infrared detector having a surface sensitive to infrared radiation emanating from said heated surface portion.

42. A method as claimed in claim 41, wherein said infrared detector comprises a InSb photodiode.

43. A method as claimed in claim 41, wherein said surface portion is heated by a laser beam travelling along an optical path and directed onto said surface portion, said laser beam passing through a dichroic mirror disposed in the optical path thereof, and wherein a center point of the heated surface portion is reflected by said dichroic mirror and imaged onto the surface of said infrared detector by means of an imaging lens positioned intermediate said dichroic mirror and said infrared detector.

44. A method as claimed in claim 40, wherein said noncontact temperature sensing means comprises a HgCdTe photodiode.

45. A method as claimed in claim 40, wherein said noncontact temperature sensing means comprises a thermopile.

46. A method as claimed in claim 40, wherein said noncontact temperature sensing means comprises a pyroelectric detector.

47. A method as claimed in claim 35, wherein step (c) is performed by providing a curve of the measured power values against time, said curve having a shape related to the degree of cure of said polymeric composite, and evaluating said degree of cure from the shape of said curve as compared with said calibration reference.

48. A method as claimed in claim 47, wherein said heated surface portion is allowed to cool to near ambient temperature, and steps (a) through (c) are repeated at least once with the cooled surface portion being re-heated and maintained at the same constant temperature to obtain at least one further curve serving as said calibration reference.

49. A method as claimed in claim 35, wherein said polymeric composite is a graphite-epoxy composite and wherein said surface portion is maintained at a constant curing temperature of about 275° C.

50. An apparatus for evaluating the degree of cure in a polymeric composite, which comprises:
heating means for heating a surface portion of the polymeric composite to substantially curing temperature;
non-contact temperature sensing means for measuring the temperature of the heated surface portion to provide output signals representative of the surface temperature values;
a feedback circuit connected between said heating means and said temperature sensing means, said feedback circuit having control means for controlling said heating means in response to the output signals provided by said temperature sensing means so as to maintain said curing temperature constant over a predetermined period of time;
monitoring means connected to an output of said control means for continuously monitoring the amount of powder required to maintain said heated surface portion at said constant temperature during said predetermined period of time, thereby obtaining data comprising power values measured as a function of time; and
means for processing said data including comparing with a calibration reference to obtain an evaluation of the degree of cure of said polymeric composite.

51. An apparatus as claimed in claim 50, wherein said heating means comprises a laser source operative to generate a laser beam directed onto said surface portion for heating same.

52. An apparatus as claimed in claim 51, wherein said laser source is an argon-ion or $CO_2$ laser source.

53. An apparatus as claimed in claim 50, wherein said heating means comprises a heat lamp.

54. An apparatus as claimed in claim 53, wherein said heat lamp is a quartz-halogen lamp.

55. An apparatus as claimed in claim 50, wherein said non-contact temperature sensing means comprises an infrared detector having a surface sensitive to infrared radiation emanating from said heated surface portion.

56. An apparatus as claimed in claim 55, wherein said infrared detector comprises a InSb photodiode.

57. An apparatus as claimed in claim 55, wherein said heating means comprises a laser source operative to generate a laser beam travelling along an optical path and directed onto said surface portion, and wherein a dichroic mirror is disposed in the optical path of said laser beam for reflecting the infrared radiation emanating from the heated surface portion onto the surface of said infrared detector.

58. An apparatus as claimed in claim 50, wherein said non-contact temperature sensing means comprises a HgCdTe photodiode.

59. An apparatus as claimed in claim 50, wherein said non-contact temperature sensing means comprises a thermopile.

60. An apparatus as claimed in claim 50, wherein said non-contact temperature sensing means comprises a pyroelectric detector.

61. An apparatus as claimed in claim 57, wherein an imaging lens is positioned intermediate said dichroic mirror and said infrared detector for imaging onto the surface of said infrared detector a center point of said heated surface portion reflected by said dichroic mirror.

62. An apparatus as claimed in claim 50, wherein said control means comprises a proportional-integral-derivative programmable controller.

63. An apparatus as claimed in claim 50, wherein said polymeric composite is a graphite-epoxy composite and wherein said heating means together with said control means are operative to maintain said surface portion at a constant curing temperature of about 275° C.

* * * * *